United States Patent
Bordes

[11] Patent Number: 5,839,897
[45] Date of Patent: Nov. 24, 1998

[54] DRILL FOR THE INSERTION OF A DENTAL IMPLANT

[76] Inventor: Sylvain Bordes, 109, cours de la République, Mestras F 33470, France

[21] Appl. No.: 513,932
[22] PCT Filed: Feb. 28, 1994
[86] PCT No.: PCT/FR94/00224
§ 371 Date: Aug. 31, 1995
§ 102(e) Date: Aug. 31, 1995
[87] PCT Pub. No.: WO94/20247
PCT Pub. Date: Sep. 15, 1994

[30] Foreign Application Priority Data

Mar. 1, 1993 [FR] France .................................. 93/02620

[51] Int. Cl.$^6$ .................................................. A61C 3/02
[52] U.S. Cl. .......................................... 433/165; 408/144
[58] Field of Search .................................... 433/165, 166; 408/226, 227, 229, 231, 232, 144, 713

[56] References Cited

U.S. PATENT DOCUMENTS

| | | | |
|---|---|---|---|
| 3,460,410 | 8/1969 | Briles | 77/72 |
| 3,991,454 | 11/1976 | Wale | 408/226 |
| 4,135,847 | 1/1979 | Hemmings | 408/226 |
| 4,526,541 | 7/1985 | Hubschmid | 433/165 |
| 5,035,618 | 7/1991 | Katz et al. | 433/165 |
| 5,100,267 | 3/1992 | Salyer | 407/54 |
| 5,429,504 | 7/1995 | Peltier et al. | 433/165 |
| 5,435,722 | 7/1995 | Mandell | 433/165 |
| 5,489,208 | 2/1996 | Mandell | 433/165 |
| 5,494,382 | 2/1996 | Kloppers | 408/226 |

FOREIGN PATENT DOCUMENTS

A-1602794 12/1970 Germany.
2086279 10/1981 United Kingdom ............ B23B 51/00

*Primary Examiner*—Cary E. O'Connor
*Attorney, Agent, or Firm*—Blakely Sokoloff Taylor & Zafman

[57] ABSTRACT

A drill for the insertion of a dental implant is disclosed. The drill includes a rotational drive portion in the form of a metal rod with a first end and a second end. The first end is connected to a drilling apparatus. The second end of the rotational drive portion is connected to an active cutting portion made of plastic overmolded on a second end of the metal rod. The drill further includes a metal insert portion coupled to the active cutting portion to serve as a sharp edge for the active cutting portion.

6 Claims, 2 Drawing Sheets

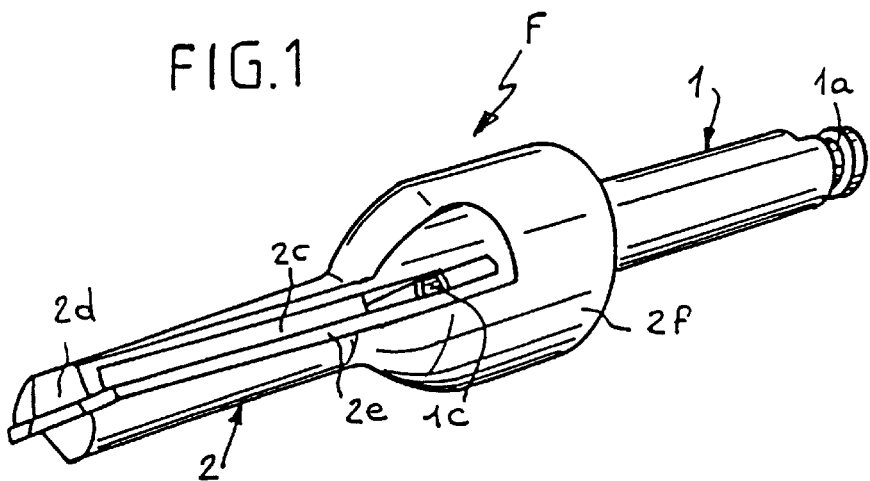
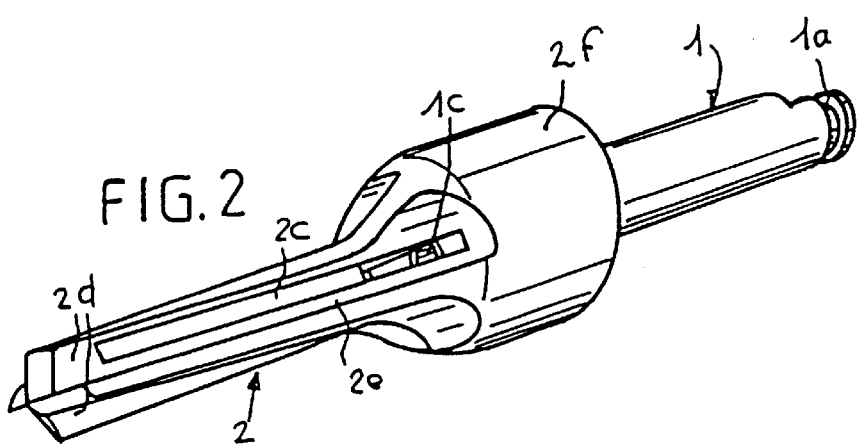
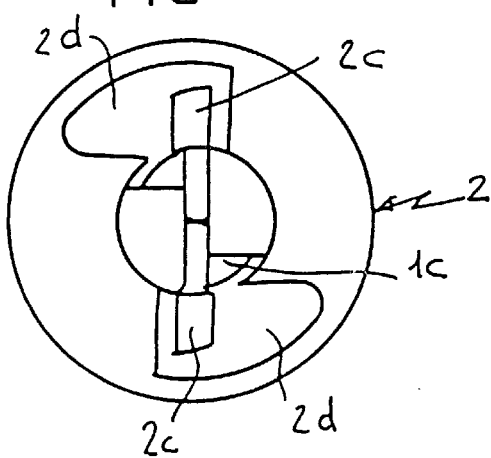
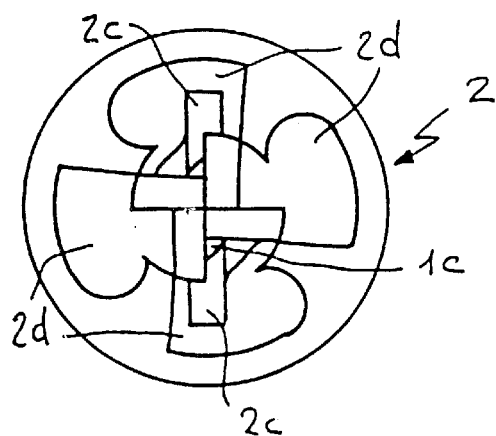

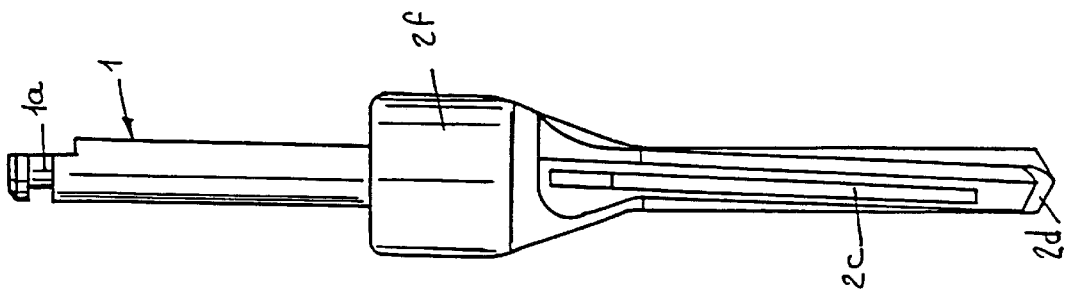
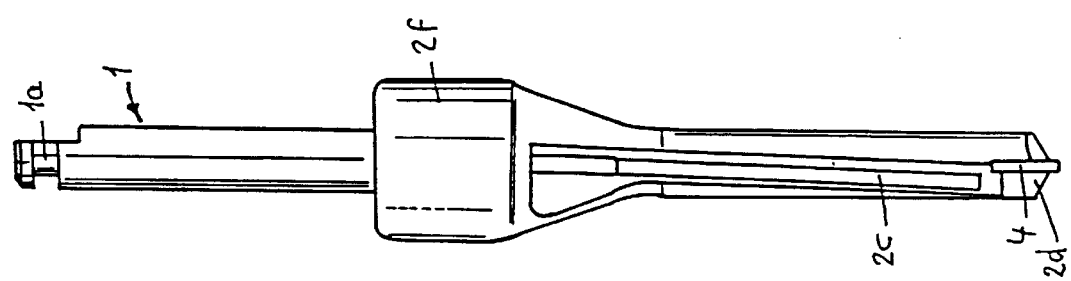
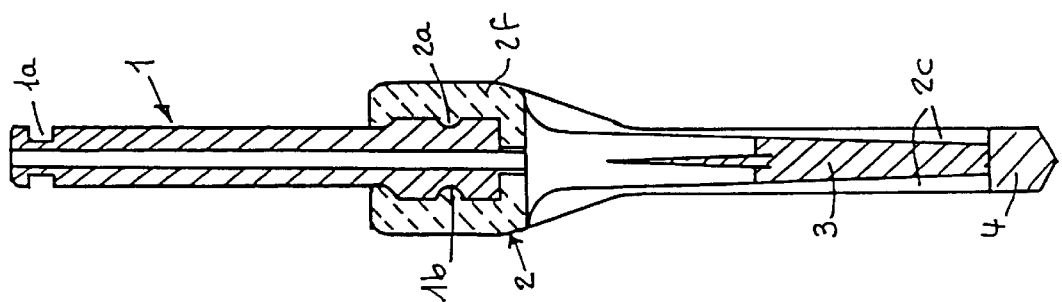
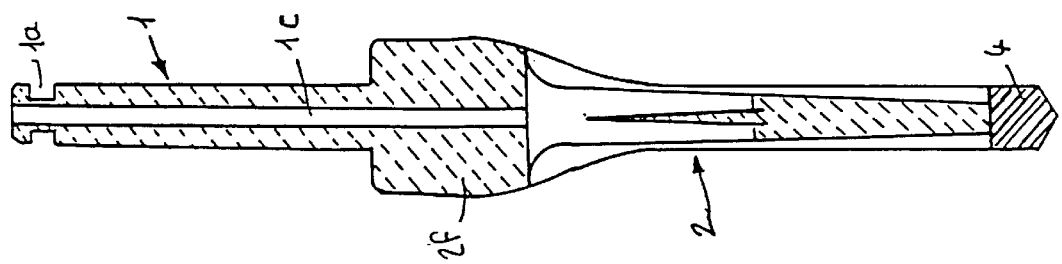

DRILL FOR THE INSERTION OF A DENTAL IMPLANT

A dental implant generally comprises a body impacted in the alveolar bone. For this impaction, it is necessary to carry out a drilling of the bone by means of a drill. The drills employed for this type of operation are made of metal, especially of stainless steel, and constitute monobloc assemblies.

The cost of these drills is high in view of the nature of the materials from which they are made and of the need for special machining in order to form the cutting edges. This cost is found to be an important factor, given that for each implant there is a specially-adapted instrumentation.

Furthermore, in order to reuse such tools, it is necessary to sterilize them in view of their application and thereby to avoid any risk of contamination. It is thus obligatory, upon each use, to carry out particularly meticulous cleaning and sterilization.

In addition, these repeated uses inevitably lead to wear of the tool and, consequently, to a decrease in effectiveness.

The invention is based on the object of remedying these drawbacks in a straightforward, reliable, effective and rational manner.

The problem which the invention proposes to solve is that of proposing a drill of reduced cost which can be disposed of after each use, thereby obviating the cleaning and sterilization operations, and consequently ensuring its sterile nature upon each use.

In order to solve such a problem, and in a first embodiment, a drill has been designed and developed which comprises a portion, in the form of a rod, for connection to an apparatus of the drilling machine type, and an active cutting portion, said portions constituting a monobloc disposable plastic assembly.

In another embodiment, the drill comprises a portion, in the form of a rod, for connection to an apparatus of the drilling machine type, and an active cutting portion, said portions being independent, the rod being made of stainless steel, and the active portion being made of plastic, and they have complementary arrangements so that they can be assembled by overmolding with a view to forming a disposable assembly.

In order to solve the given problem of increasing the cutting efficiency and the hardness of the active portion, the latter has a metal insert serving as a sharp edge.

It is also proposed that the end of the active portion has a metal cutting tip attached to and embedded in the plastic.

In order to solve the given problem of avoiding any heating of the bone, the connection portion has a bore for the passage of a lubricating fluid, the hole opening out into at least one channel formed in the active portion for directing the fluid as far as the point of the drill.

The active cutting portion has, longitudinally, helical flukes into which the channel or channels open.

In order to increase the rigidity of the drill assembly and to avoid any shearing effect, the active portion has, in the area of its connection to the rod, a cylindrical span of greater diameter.

The invention is explained in greater detail hereinafter with the aid of the attached drawings, in which:

FIG. 1 is a perspective view of one embodiment of the drill according to the invention.

FIG. 2 is a perspective view of another embodiment of the drill according to the invention.

FIG. 3 is a view in longitudinal section of the drill in the case where the latter is made entirely of plastic.

FIG. 4 is a view in longitudinal section of another embodiment of the drill.

FIG. 5 is a view in transverse section, on a larger scale, seen along the line 5.5 in FIG. 1.

FIG. 6 is a view in transverse section, on a larger scale, seen along the line 6.6 in FIG. 2.

FIG. 7 is a front view of the drill corresponding to the embodiment illustrated in FIG. 1.

FIG. 8 is a front view of the drill corresponding to the embodiment illustrated in FIG. 2.

The drill designated overall by (F) comprises a connection portion (1) in the form of a rod, and an active cutting portion (2). The portion (1) is designed at its free end (1*a*) so as to be coupled to any type of apparatus of the drilling machine type.

In the embodiment illustrated in FIG. 3, the portions (1) and (2) constitute a monobloc assembly obtained in particular by injection molding of plastic, in order to constitute a disposable drill.

In the embodiment illustrated in FIG. 4, the two portions (1) and (2) are independent. The portion (1) constitutes a stainless steel rod. The portion (2) is made of plastic. The portions (1) and (2) have complementary arrangements (1*b*) and (2*a*) in order to be assembled by overmolding. For example, these arrangements consist of peripheral channels formed at the end of the rod (1) constituting zones for retention of the active portion (2). With this solution, the drill also constitutes a disposable assembly.

In this embodiment, the active portion (2) can have a metal insert (3) serving as a sharp edge.

Irrespective of the mode of execution of the drill, that is to say constituting a monobloc assembly made entirely of plastic (FIG. 3) or else an assembly simultaneously including portions made of plastic and portions made of metal, the end of the active portion (2) can have a cutting tip (4). This cutting tip is over-molded with the plastic of the active portion (2) and is made of metal, in particular titanium.

In accordance with another characteristic, the rod (1) is bored longitudinally at (1*c*) for the passage of a lubricating fluid. This hole (1*c*) opens out into at least one channel (2*c*) formed in the active portion (2) in order to direct the fluid as far as the point of the drill. Taking into account the plastic design of the active portion (2), the latter has profiled flutes (2*d*) delimiting sharp edges (2*e*).

The active portion (2) has, in the area of its connection to the rod (1), a zone (2*f*) in the form of a cylindrical span of greater diameter and connected in a tapering fashion to said portion (2). This span (2*f*) constitutes a strengthening zone.

The advantages emerge clearly from the description, and in particular we underline and reiterate:

the disposable nature of the drill upon each use, obviating any cleaning and sterilization, the internal irrigation of the drill, avoiding any heating of the bone, the cutting quality obtained by using a new drill for each operation, the reduced cost price.

I claim:

1. A drill for the insertion of a dental implant comprising:
   a rotational drive portion in the form of a metal rod with a first end and a second end, wherein said first end has a shape for coupling to a drilling apparatus,
   an active cutting portion made of plastic overmolded on said second end of the rotational drive portion, and
   a metal insert portion coupled to said active cutting portion to serve as a sharp edge for the active cutting portion.

2. The drill of claim 1, wherein said second end of said rotational drive portion includes a first coupling portion and said active cutting portion includes a second coupling portion, and wherein said first and second coupling portions are complementary in shape and substantially integrate said rotational drive portion and said active cutting portion when said active cutting portion is overmolded on said rotational drive portion.

3. The drill of claims 1 or 2, wherein the metal insert of the active cutting portion is a metal cutting tip attached to and embedded in the plastic.

4. The drill of claims 1 or 2, wherein said active cutting portion is substantially cylindrical and has a first end portion and a second end portion, wherein said first end portion is coupled to said metal rod, and wherein said first end portion has a diameter that is larger than said second end portion.

5. The drill of claim 1, wherein the metal rod is equipped with a longitudinal bore for the passage of a lubricating fluid, and wherein the bore (1c) is adjacent to at least one channel formed in the active cutting portion to convey fluid from said rotational drive portion to said active cutting portion.

6. The drill of claim 5, wherein the active cutting portion has helical flutes that extend along the longitudinal axis of said active cutting portion and into which said channel opens.

* * * * *